(12) United States Patent
Nielsen (10) Patent No.: US 6,998,509 B1
(45) Date of Patent: Feb. 14, 2006

(54) WOUND CARE DEVICE

(75) Inventor: Brian Nielsen, Goerloese (DK)

(73) Assignee: Coloplast A/S, Humlebaek (DK)

( * ) Notice: Subject to any disclaimer, the term of this patent is extended or adjusted under 35 U.S.C. 154(b) by 301 days.

(21) Appl. No.: 10/089,073

(22) PCT Filed: Oct. 4, 2000

(86) PCT No.: PCT/DK00/00557

§ 371 (c)(1),
(2), (4) Date: Apr. 8, 2002

(87) PCT Pub. No.: WO01/24840

PCT Pub. Date: Apr. 12, 2001

(30) Foreign Application Priority Data

Oct. 7, 1999 (DK) .................................... 1999 01446

(51) Int. Cl.
*A61F 13/00* (2006.01)

(52) U.S. Cl. .......................................... 602/48; 602/49
(58) Field of Classification Search ............. 602/41–59; 121/889, 885; 604/304–308; 429/443–445
See application file for complete search history.

(56) References Cited

U.S. PATENT DOCUMENTS

| | | | |
|---|---|---|---|
| 5,420,197 A | 5/1995 | Lorenz et al. ............. | 525/54.3 |
| 5,496,933 A | 3/1996 | Kelkenberg ................. | 536/20 |
| 5,599,916 A | 2/1997 | Dutkiewicz et al. .......... | 536/20 |
| 5,900,479 A | 5/1999 | Glasser et al. ................ | 536/20 |

FOREIGN PATENT DOCUMENTS

| | | |
|---|---|---|
| EP | 0 171 254 | 2/1986 |
| EP | 0 477 979 | 4/1992 |
| JP | 9-169654 | 6/1997 |
| WO | 94/16746 | 8/1994 |
| WO | 94/17227 | 8/1994 |
| WO | 97/25463 | 7/1997 |
| WO | 97/29132 | 8/1997 |
| WO | 97/30092 | 8/1997 |
| WO | 97/41900 | 11/1997 |
| WO | 98/46818 | 10/1998 |
| WO | 98/50050 | 11/1998 |

OTHER PUBLICATIONS

Chitin and Chitosan; Bae 465—Biomedical Applications of Textiles; Jun. 7, 1996.

*Primary Examiner*—Kim M. Lews
(74) *Attorney, Agent, or Firm*—Jacobson Holman PLLC (57) ABSTRACT

Wound care device comprising chitosan, said chitosan being capable of absorbing liquid to form a swollen, coherent gel, and said chitosan being in the form of fibers having been modified by treatment with acid in a solvent which is not able to dissolve the chitosan fibers and by treatment with heat.

15 Claims, 1 Drawing Sheet

Fig. 1

WOUND CARE DEVICE

This is a nationalization of PCT/DK00/00557 filed Oct. 4, 2000 and published in English.

FIELD OF THE INVENTION

The present invention relates to a wound care device comprising chitosan, said chitosan being capable of absorbing liquid to form a swollen, coherent gel, and a method of preparation of the same.

BACKGROUND OF THE INVENTION

In the treatment of exuding wounds there is a need for an absorbent dressing being capable of adapting to the conformation of the individual wound. This may be done by using fibre dressings or hydrogels.

Wound care devices comprising fibres may be based on polysaccharide fibres, which are usually water insoluble, but water absorbing. They are in general based on alginate or CMC. Wound care products such as dressings or fillers based on alginate or CMC, may be able to absorb up to 15–25 g exudate/gram product, with limited swellablity and gellability. These fibre dressings/fillers are normally supplied as sterile.

The use of fibres often suffers from the drawback of a limited absorption and/or lack of cohesion, leading to difficulties with respect to removing the fibre product from the wound as the product does not constitute a cohesive part.

Methods of preparing alginate fibres are well known. Normally sodium alginate is completely converted into insoluble calcium alginate fibres. Methods for enhancing the solubility of alginate fibres are also well known. International Patent Application No. WO 94/17227 discloses a method for preparing highly absorbent alginate fibres by conversion of calcium alginate fibres into alginic acid fibres.

In International Patent Application No. WO 94/16746 is disclosed a process of preparing carboxy methyl cellulose fibres which are gellable, but still coherent enough to be removed from a wound in one piece.

European Patent Application No. 627 225 discloses a method for preparing a superabsorbent chitosan powder, being capable of absorbing liquid many times it own weight by forming a transparent gel. This is done by treating the powderous chitosan with an acid, preferably a hydroxy carbon acid like lactic acid or hydroxy butylic acid. The resulting powder is capable of absorbing high amounts of water by forming a gel.

The acid-modified chitosan disclosed in EP 627 225 A2 is suitable for use as a superabsorbent in diapers and like products, in which the powdered material will be encapsulated and little or no coherence is demanded. However, the reference is silent with respect to preparation of highly coherent material, for use in e.g. wound care products.

Published Japanese Patent Application No. JP 9-169654-A discloses a method for preparing partly deacetylated chitin fibres for wound care. The preferred chitin material has a deacetylation degree of max. 90%, preferably 40–60%. The material is not used as an absorbent, but as a haemostatic agent for stopping bleeding wounds.

In European Patent Application No. 171 254 is disclosed chitin fibres being treated in an aqueous solution with acid and elevated temperature. The fibres remain their structure due to the fact that chitin is not soluble in an acidic aqueous solution.

Contrary to chitin, chitosan is soluble in an acidic aqueous solution.

International Patent Application No. 97/29132 discloses chitosan being dissolved in a weak acidic aqueous solution. The chitosan is treated with a carboxylic acid polyanhydride as a cross-linking agent. The resulting hydrogel may subsequently be processed into powders or fibres.

Thus, there still is a need for a wound care device comprising a material being capable of absorbing large amount of liquid by gelling, having a three-dimensional structure in the form of fibres, and having a high degree of cohesion after absorption. The need is fulfilled by the wound care device of the present invention.

BRIEF DESCRIPTION OF THE INVENTION

The present invention relates to a wound care device comprising chitosan, said chitosan being capable of absorbing liquid to form a swollen, coherent gel.

The present invention further relates to a method of preparation of a wound care device comprising chitosan being capable of absorbing liquid to form a swollen, coherent gel.

DETAILED DESCRIPTION OF THE INVENTION

The invention relates to a wound care device comprising chitosan, said chitosan being capable of absorbing liquid to form a swollen, coherent gel, and said chitosan being in the form of fibres having been modified by treatment with acid in a solvent which is not able to dissolve the chitosan fibres and by treatment with heat.

The fibrous structure of the chitosan according to the present invention may provide a essential coherence for use in a wound dressing. When used as e.g. a wound contacting fabric, it is important that the absorbent material is coherent rendering it possible to remove the wound dressing in one piece from the wound.

A fibre is in this application defined as an elongated member wherein the proportion between length and diameter of the member is at least 25. This definition includes filaments as well.

Chitosan fibres may be used as raw material. In principle, all types of chitosan fibres may be used. The preparation of the modified chitosan fibres according to the invention may be optimised depending on the quality of the raw material. Parameters such as fibre diameter, molecular weight of chitosan, degree of deacetylation and source or origin of the chitosan may influence on the process. Chitosan fibres are usually made from chitosan of a relatively low molecular weight.

It is preferred that the molecular weight of the chitosan used for the preparation of the wound care device according to the present invention is less than 750.000, more preferred less than 400.000, and even more preferred less than 250.000, and most preferred less than 175.000.

Most preferred is chitosan with a molecular weight lower than 300.000.

Chitosan fibres suitable for use in this invention are fibres with a deacetylation degree above 65%, more preferred above 75% and most preferred above 85%.

The viscosity of the chitosan used according to the invention may preferably be less 1000 cP, more preferred less than 500, even more preferred less than 300. The most preferred viscosity is from 40 to 200 cps. The viscosity is measured on a 1% w/w chitosan dissolved in an aqueous solution of 1% w/w acetic acid on a Brookfield LVT viscometer, 25° C., appropriate spindle at 30 rpm.

Preferably, the fibres are having a minimum average length of 3 mm. The preferred proportion between length and diameter of the fibres is at least 25, more preferred at least 80 and most preferred at least 200.

The invention also relates to a method of preparation of a wound care device comprising chitosan being capable of absorbing liquid to form a swollen, coherent gel, said method comprises the steps of
a) suspending the chitosan in the form of fibres in a non-solvent comprising acid
b) isolating the resulting modified chitosan fibres from the non-solvent
c) treating the chitosan fibres with heat during step a) or/and b).

The chitosan is according to the present invention modified by treatment with acid and heat. This treatment is converting the chitosan fibres from a water insoluble, non swelling and non gelling state into chitosan fibres which are water swelling, water gelling but still substantially water insoluble and with a coherent structure.

By the terms water swelling, water gelling but substantially water-insoluble is meant that when the fibres are contacted with an aqueous liquid, such as wound exudate, they will absorb liquid and swell by forming a gel. The fibre structure will still be detectable. The fibres will turn from non-transparent into relative transparent fibres. The fibres are not completely water-insoluble (few molecules may dissolve), but the material is sufficient water-insoluble and coherent to render it possible to remove the fibres from a wound in one piece.

The non-solvents used according to the present invention may be any non-solvent to chitosan. Preferably, the non-solvent has a boiling point higher than 50° C. and even more preferred a boiling point between 60 and 250° C.

Suitable acids for this embodiment of the invention may be any low molecular organic acid.

The preferred acids are organic acids such as formic, acetic, halogen acetic acids (such as fluoro or chloro acetic acid), propanoic, propenoic, lactic, acrylic glyoxylic, pyruvic or a hydroxy propionic/butanic acid.

The more preferred organic acids used for modification of the chitosan fibres in the wound care device according to the invention may be a hydroxy or acyl organic acid, which is soluble in the used non-solvent, preferably glucolic, glyoxylic, pyruvic, lactic or a hydroxy propionic/butanic acid.

The most preferred acid is lactic acid.

Preferably, the quantity of acid used in the modification process according to the present invention is from 2 mmol to 20 mmol per gram chitosan, more preferred from 3 to 15 mmol acid per gram chitosan and most preferred from 4 to 10 mmol acid per gram chitosan. Higher amounts of acid will not change the result in neither a positive nor negative way, and is therefore considered to be unnecessary.

The heat treatment of the chitosan fibres may be conducted at any temperature above 50° C.

The preferred temperature of the heat treatment of the chitosan fibres is between 50–250° C., more preferred from 60 to 225° C.

The modified fibres according to this invention have preferably an absorption higher than 20 g/g, more preferred higher than 25 g/g and most preferred higher than 30 g/g.

The wound care device according to the invention may be in the form of a fibre rope, woven, knitted or non-woven sheets or pouches or it may be in the form of an island dressing, with an absorbent centre part based on the modified chitosan fibres and an adhesive film covering and extending further than the absorbent part.

The wound care device according to the invention may be based on a woven or non-woven fabric comprising the modified chitosan fibres, which is water swellable and gellable.

The wound care device may have a minimum absorption of 0.20 g/cm2.

The absorption of the wound care device according to the invention is preferably minimum 0.20 g/cm2, more preferred minimum 0.25 g/cm2 and most preferred more than 0.30 g/cm2.

If the modified chitosan fibres are preferably in the form of a wound cavity filler such as a fibre rope, the total absorption of the rope is more than 20 g/g, preferred more than 25 g/g and most preferred more than 30 g/g.

The wound care device according to the present invention is especially suitable for treatment of leg ulcers, burns, pressure sores, diabetic ulcers, cancer wounds and acute wounds.

In a first embodiment of the invention the acid treatment and the heat treatment is a combined process, according to which the chitosan fibres may be treated with acid under simultaneous heat treatment.

In the first embodiment of the invention the temperature of which the acid treatment is processed is preferably from 50 to 200 more preferred from 60 to 180° C. and most preferred from 64 to 160° C.

In a second embodiment of the invention, the acid is a mixture of at least two acids.

The first acid may be a hydroxy organic acid, which is soluble in the used solvent, preferably glucolic or a hydroxy propionic/butanic acid. Especially preferred is lactic acid.

When chitosan molecules are treated with acids of the first type at a temperature below 85° C., very weak and few crosslinking point between the chitosan molecules are created. This will turn the chitosan from an insoluble form into almost soluble form with very limited cohesion. If the material is sterilised by radiation this will result in an even lower cohesion. Thus, there is a need for additional cohesion. This may be obtained by adding the second type of acid to the treatment.

The first acid is imparting gelling and swelling ability to the chitosan fibres and the second acid is imparting cohesion to the fibres.

The second acid will provide the fibres with substantially insolubility and cohesion. The cohesion may be obtained as a result of intermolecular cross-linking between the chitosan molecules, where the chitosan molecules may form an acid salt with the second acid.

The second acid may be an inorganic sulphur or phosphor acid or any organic acid except hydroxy acids, which is soluble in the used non-solvent. Preferred organic acids may be: Formic, acetic, propanoic, butanoic and propenoic acid. Also halogenated derivative of these such as chloro acetic acid may be used.

It is preferred that the second acid is an inorganic sulphur or phosphor acid or one of following organic acid: Formic, acetic, propanoic, butanoic and propenoic acid, or a halogenated derivative of these such as chloro acetic acid.

It is especially preferred that the second acid is formic, acetic, propanoic or propenoic acid.

The first acid may comprise 20–100% of the total acid content, more preferred 40–97% and most preferred 60–95% of the total acid content.

The second acid may comprise 0–80% of the total acid content of the solution, more preferred 3–60%, and most preferred 5–50% of the total acid content.

It is preferred to let the acid treatment last until the desired level of cross-linking occurs. By reducing the reaction time of the process, the chitosan fibres may have been converted to a chitosan acid salt, but the molecules have not yet crosslinked. This results in more or less water soluble chitosan fibres, which is not desired.

The process time for the combined acid and heat treatment may suitably be more than 0.5 hours, preferably more than 4 hours, dependent on the temperature of the heat treatment.

If the treatment is prolonged to more than 4 hours, it may be possible to use only acid of the first type, especially if the temperature is below to 85° C., and still obtain a highly cohesive wound care device.

By combining the above specified first and second acid in the specified amount, the resulting fibres are water swellable and gellable, but still water insoluble rendering it possible that a wound care dressing comprising these modified chitosan fibres may be removed in one piece after having absorbed wound exudate.

Combinations of acids within each group of either first or second acid group may also be applied.

Especially preferred is a mixture of lactic acid and any low molecular weight organic acid (molecular weight<300 g/mole).

Most preferred is an acid mixture of lactic acid and formic, acetic, propanoic or propenoic acid.

The combined acid and heat treatment of the chitosan in this embodiment of the invention may be conducted at a temperature of 50–85° C., more preferred from 60 to 85° C., even more preferred from 64 to 85° C. and most preferred at the boiling point of the non-solvent.

In a third embodiment of the invention, the acid treatment is conducted at a high temperature, above 85° C. When the temperature is kept above 85° C. in the acid treatment, only one acid is necessary to achieve the preferred properties of the chitosan fibres.

The preferred acid used in the modification of the chitosan fibres of this embodiment of the invention is an hydroxy organic acid, which is soluble in the used solvent, preferably glucolic or a hydroxy propionic/butanic acid.

Especially preferred is lactic acid.

Mixtures of acids may also be used.

The temperature at which the treatment is conducted is preferably from 85 to 200° C., more preferred from 85 to 180° C. and more preferred from 85 to 160° C. and most preferred form 90 to 160° C.

The used non-solvent can be any non-solvent, preferably with a boiling point above 85° C. Most preferred is alcoholic solvents such as propanol, isopropanol and butanol.

The duration of the acid treatment depends of the type and quantity of acid, the quantity of water and the temperature. The process time may vary from seconds to several hours. The higher temperature and quantity of acid and water, the shorter time is needed to achieve the desired properties of the chitosan fibres.

The higher concentration of acid during the acid treatment, the shorter time is needed to convert the chitosan fibres.

In a fourth embodiment of the invention, the acid treatment is not conducted at an elevated temperature. After the acid treatment, the fibres are isolated from the acid solution and subsequently subjected to a heat treatment, e.g. in an oven, at an elevated temperature.

In general, the acid treatment will turn the chitosan fibres from insoluble and low absorbent into water soluble, or if the acid treatment is limited, partly soluble and partly water insoluble. The solubility is a consequence of that the chitosan molecules are in the acid treatment converted to chitosan acid salts molecules. Therefore the acid treatment influences the subsequent heat treatment and the performance of the modified fibres.

Acids suitable for this embodiment of the invention are low molecular weight inorganic acids and organic acids such as formic, acetic, halogen acetic acids (such as flouro or chloro acetic acid), propanoic, propenoic, lactic, acrylic, glyoxylic, pyruvic or a hydroxy propionic/butanic acid, more preferred organic acid such as formic, acetic, propanoic, propenoic, lactic, acrylic, glyoxylic, pyruvic or a hydroxy propionic/butanic acid.

Most preferred is lactic acid.

In this embodiment of the invention one acid or a mixture of two or more acids may be used. Mixtures may be any suitable mixture such as lactic acid and any low molecular weight organic acid (molecular weight below 300 g/mole and soluble in the non-solvent).

The temperature during the acid treatment should be kept so low, that the fibres do not form a gel after the treatment but dissolve when they are contacted with water.

The temperature during the acid treatment is preferably from the freezing point of the solvent and up to 80° C., depending on what temperature the fibres start to gel. The temperature is more preferred kept from −10 to 64° C., and even more preferred kept at −10 to 40° C., and most preferred kept at room temperature.

The duration of the acid treatment should be until a sufficient numbers of amine groups have been protonated so the chitosan fibres will form a gel after the heat treatment if contacted with an aqueous liquid. The duration of the acid treatment depend on the amount of water, type of acid, amount of acid and the type, shape or origin of the chitosan.

The size of the chitosan fibres is also important. The larger diameter of the fibres, the longer acid treatment time is needed.

The duration of the acid treatment may, depending on the water amount, acid concentration, temperature and chitosan fibres be treated from a few seconds to many hours before the treatment is ended.

If the acid treatment is carried out with 6% water, ethanol and 7.5 mmol acetic acid per gram chitosan fibres (100 gram non-solvent per 10 gram chitosan fibres), the acid treatment of the chitosan fibres will after only 10 minutes acid treatment at room temperature be almost completely soluble in water.

After the acid treatment the fibres may be washed in an alcohol to remove residual acid, and subsequently dried.

Hereafter the fibres may be subjected to a dry heat treatment. The heat treatment may be carried out at an elevated temperature, preferably from 60 to 250° C., more preferred 80 to 250° C. and most preferred at 100 to 200° C.

During the heat treatment, the chitosan fibres will turn from water soluble to water swellable, gellable and substantially water insoluble.

The duration of the heat treatment depends on the temperature of the heat treatment and the choice of acid. If the dry heat treatment is carried out at 100° C., the heat treatment has a duration of preferably 0.5 to 8 hours, depending on which acid is used. The higher temperature in the heat treatment, the shorter time is needed to convert the fibres from water soluble to swellable, water absorbent and gellable. If the heat treatment is carried out at 175° C. only a few minutes or even seconds are needed to convert the fibres to gellable and more insoluble.

The more severe heat treatment, the less swellable the fibres becomes. The more gentle heat treatment, the more swellable becomes the fibres, and optionally water soluble. Therefore the heat treatment should be optimised so the chitosan fib es after the heat treatment are water swellable and substantially water insoluble.

In this embodiment of the invention, it is preferred to conduct the acid treatment at room temperature with 4 to 10 mmole acid, e.g. 80% lactic acid and 20% acetic acid, per gram chitosan, rinse the fibres in ethanol and heat treat the fibres at 160 ac in 10 minutes. The fibres are processed into a non-woven fabric, packed and sterilised.

In a fifth embodiment of the invention the chitosan fibres are first treated with acid, and subsequently treated with a base. In this way, the fibres are first converted to water soluble fibres by the acid treatment, and are then turned into water swellable but substantially water insoluble absorbent fibres by the alkaline treatment.

In a sixth embodiment of the invention, the chitosan fibres are treated with heat both during the acid treatment and then again subsequently.

In a seventh embodiment of the invention the amount of acid used is insufficient for a complete conversion of the chitosan, resulting in fibres which are water swellable, water gelling but substantially water insoluble. The resulting chitosan fibres will thus comprise non-modified parts where the absorption is lower but the cohesion is higher than in the parts where the chitosan is fully converted. This combination may reduce the risk of gel-blocking in the fibrous material, as well as the higher cohesion may ease the further processing and handling of the fibres.

By treated in such a limited way is meant, that the chitosan fibres may only be partly converted into a acid salt, in such a manner that the molecules will expand when they contacted with an aqueous liquid, but still maintain their structure in such a degree, that removal in one piece from a wound is possible. The process of carrying out this embodiment of the invention is preferably by reducing amount of acid in the acid treatment. By doing this, the acid will not be able to complete the conversation of chitosan into a chitosan salt.

In this embodiment the fibres may be treated as in the first and the second embodiment of the invention, but only with a minimal amount of acid. The amount of acid is from 2 to 7.5 mmole acid per gram chitosan preferably 3–7.5 mmole acid per gram chitosan and most preferred from 5 to 7 mmole acid per gram chitosan.

The fibres are optionally treated with acids of the first type. The most preferred acid is lactic acid.

In an eighth embodiment of the invention, the used chitosan fibres are "never-dried" chitosan fibres. By using "never-dried" chitosan fibres, the process for modifying the fibres may be adjusted in such a manner, that water absorbent, gellable and substantially water insoluble fibres still may be obtained after the modification process. This is preferably done by treating the fibres more gentle than if dried fibres were used in the modification process.

Another way of improving the strength of the chitosan fibres, is coating or impregnating an anionic material onto the modified fibres. Anionic polysaccharides such as carboxy methyl cellulose (CMC), alginate, carrageenan or pectate may be preferred as coating or impregnation material.

In a ninth embodiment of the invention strength is added to the modified chitosan fibres by adding anionic fibres.

In a wound care device more strength and cohesion may be desired. This may be obtained by adding fibres other than chitosan to the device. These fibres may be blended with the chitosan fibres or be woven, or be in separate layers.

These anionic fibres may be fibres such as alginate or carboxy methyl cellulose fibres. When the anionic fibres are added to the modified chitosan fibres, they will, when the fibres are contacted with wound exudate, open up their structure and a crosslinking between the anionic molecule group and the modified chitosan molecule group will occur.

The amount of anionic fibres in a wound care device according to the present invention is preferably between 5 and 60% and more preferred between 10 and 50%.

The process of adding anionic fibres could be any suitable process, one example of such a process could be by carding both the modified chitosan and the anionic fibres into a carded fibre mixture.

An other way of manufacturing could be to make yarn of both the modified chitosan and the anionic fibres and weave the fibres into a woven fabric.

In a tenth embodiment of the invention, the modified chitosan fibres are mixed with unmodified chitosan, cotton, wool or viscose fibres or the like, and processed into a woven or non-woven fabric, obtaining a product which is water insoluble and low absorbent cotton, wool or viscose and water gellable, water swellable, highly water absorbent and substantially water insoluble modified chitosan fibres.

The above mentioned fabric may be manufactured by mixing the chitosan and the other fibres before or after the modification of the chitosan. The fibres may be spun into a yarn of e.g. cotton and chitosan, comprising preferably 5–95% modified chitosan and more preferably 10–90% modified chitosan, and most preferred 25–75%, depending on the use of the fabric.

If the fabric is to be used for low exuding wounds, a dressing with a low amount of modified chitosan fibres is desired, but if the fabric is to be used on highly exuding wounds, a higher amount of modified chitosan fibres is requested. The process of preparing this embodiment of the invention may be the same process as described in the 9th embodiment of the invention.

An other process of preparing the wound care device may be to process chitosan fibres into yarn and then modify the chitosan yarn to obtain yarn of modified chitosan. The yarn is weaved with any of the above described nonionic fibres.

In both the ninth and the tenth embodiment of the invention less cohesive modified chitosan fibres may be used, as the added non modified chitosan fibres will provide strength and cohesion to the resulting wound care device.

In an eleventh embodiment of the invention the chitosan material may be present in the form of powder, then first modifying chitosan powder with acid and heat, and then process the modified powder particles into fibres. The modified fibres are subsequently processed into a wound care device.

In a twelfth embodiment of the invention the modified chitosan fibres are processed into a non-woven fabric. The non-woven fabric may be formed by randomly laying, for example dry-laying, and/or cross-laying the fibres followed by needling. Alternatively a non-woven fabric may be formed by cross-laying the modified chitosan fibres while partially moist, followed by drying, optionally under pressure.

The non-woven product may be used as a wound dressing or as a wound contacting layer of a wound care product.

In a thirteenth embodiment of the invention the wound care device comprises one or more active ingredients, e.g. a pharmaceutical medicament. This opens for a combined medical treatment of a wound, where the fibres absorb wound exudate and the pharmaceutical medicaments will be applied to the wound. The pharmaceutical medicaments will either be incorporated in the wound care device or migrate to the wound surface and promote its function.

Examples of such pharmaceutical medicaments includes a cytochine such as a growth hormone or a polypeptide growth factor such as TGF, FGF, PDGF, EGF, IGF-1, IGF-2, colony simulating factor, transforming growth factor, nerve stimulating growth factor and the like giving rise to the incorporation of such active substances in a form being apt to local application in a wound in which the medicament may exercise its effect on the wound, other medicaments such-as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chincho-caine, emollients, retinoids or agents having a cooling effect which is also considered an aspect of the invention.

In a fourteenth embodiment of the invention, the chitosan fibres are partly carboxy methylated, and due to this turned from insoluble and low absorbent and into highly absorbent, gelling and substantially water insoluble. This is achieved by treating the chitosan fibres with a water/alcohol solution containing sodium hydroxide and the sodium salt of chloro acetic acid. The treatment is carried out at an elevated temperature.

The temperature and time of the treatment will depend of the concentration of the sodium hydroxide, % water and the sodium salt of chloro acetic acid. However a preferred temperature for the treatment may be 40 to 180° C., more preferred 50 to 140 and most preferred 50 to 120° C.

The duration of the treatment depends on the process parameters, however the preferred reaction time is from 1 minute to 24 hours.

If the fibres are completely carboxy methylated, the fibres will become water soluble and thus not useful as such in a wound care dressing demanding coherence. Therefore it is important that the chitosan fibres only are partly carboxy methylated, so the chitosan fibres become water absorbent, water swellable and substantially water insoluble.

The preferred degree of carboxy methylation should be between 0.1 and 0.9, more preferred from 0.25 to 0.75 and most preferred from 0.3 to 0.6 (the number refers to how many carboxy methyl units there are per monosaccharide).

The process of partly carboxy methylating chitosan fibres could be any suitable process, such as treating the chitosan fibres with a mixture of an alcohol, water, sodium hydroxide and the sodium salt of chloro acetic acid.

The invention is explained more in detail in the working examples below disclosing embodiments and properties of the wound care device of the invention. It is evident that many variations may be made without diverging from the invention the scope of which is set forth in the appended claims.

EXAMPLES

Method of Measuring Absorption of Free Fibres in Water

A weighted (W1) amount (app. 0.2 grams) of the fibre sample was cut and put into a bag made of polyethylene net. Then the sample was placed in a vessel containing excess amounts of solution A (142.5 mM NaCl and 2.5 mM $CaCl_2$). After one hour the sample was removed from the solution and held over the solution for ½ minute, whereafter the weight was measured (W3) and the sample was returned into the vessel. After 24 hours, again the weight of the sample was measured as before (W4). The weight of a wet, empty PE-net bag was also measured (W2). W2 is a average value of 10 measurements.

The absorption of the fibre sample was calculated as:
Absorption after 1 hour (g/g):
   (W3-W2-W1)/W1
Absorption (after 24 hours) in g/g:
   (W4-W2-W1)/W1

The Absorbency of a Non-Woven Fabric:

A piece of 4×4 cm was cut and weighted (W1). The sample was put into a petri dish containing excess solution A for 4 hours. Hereafter the sample was removed and allowed to drip off for ½ minute, whereafter the weight was measured (W2).

The absorption (in $g/cm^2$) was calculated as:
   (W2-W1)/16

Cohesion of the Modified Chitosan Fibres:

This test method is a qualitative measurement of the gellability, solubility and cohesion of wet fibre samples.

A fibre sample was soaked saline water (solution A) for 24 hours. After the 24 hours, the sample was qualitatively evaluated and categorised into one of following categories:

0 The sample is completely water soluble. The absorption is not measurable as the sample dissolves out of the PE-net.
1 The sample is almost water soluble with only limited gellability. The cohesion of the gel is extremely low. The absorption may be measurable, but still some parts of the sample may have dissolved out of the PE-net.
2 The sample is partly water swellable and partly gellable. Some chitosan molecules seems to dissolve (the gel is greasy). The fibre structure is slightly visible after absorption. The gelled mass has some cohesion, so removal in one piece may be possible.
3 The sample is gelled. The fibres are cohesive, water swellable and transparent The gelled fibres still maintain their fibre structure and removal in one piece is easy to obtain. The fibres are no longer greasy.
4 The sample is partly gellable and partly water insoluble. The sample is more transparent than untreated fibres and have a very high cohesion. If pressure is put on the fibres, clear fibres, "dry fibres", can be seen. It may be possible to separate single fibres from the sample.
5 The sample is water insoluble with only minimal swellability.

In the wound care device according to the present invention the preferred cohesion of the modified chitosan fibres are in the area of 2 or 3 in the above categories. If a modified fibre sample evaluate to 2 or 3, removal in one piece seems to be possible.

Materials Used in the Examples:

Chitosan fibres from R C Bio-chemical Co. Ltd., Pusan, South Korea (The fibres have a degree of deacetylation of above 90%) Chitosan powder (TM 370, particles<100 micro) from Primex ingredients, Norway
100% acetic acid (glacial) from Merck.
90% lactic acid from Merck.
Sodium hydroxide from Merck.

Calcium alginate fibres (SeaSorb filler) from Coloplast A/S, Denmark
Carboxy methyl cellulose fibres (Aquacel) from ConvaTec, Ltd, UK.
Destilled water.
96% Ethanol from Danisco, Denmark.
1-Propanol from Merck.
1-Butanol from Merck.
Solution A (142.5 mM NaCl and 2.5 mM $CaCl_2$ in distilled water).

Example 1a
Chitosan Fibres Treated with Combined Acid and Heat

In a reaction vessel 200 grams of 96% ethanol was mixed with 12 grams of water and 150 mmole acid. To this solution 20 grams of chitosan were added and the suspension was treated at the boiling point of the suspension for app. 4 hours under reflux. The fibres were then washed twice in ethanol. Each sample was sterilised by 1*30 kGy electron beam. Hereafter the absorption and cohesion of the fibres were measured.

Table 1 is showing the absorption and cohesion of the samples, measured on sterilised samples. The absorbency was measured as double measurements.

TABLE 1

| Sample | Mole % acetic acid* | Absorption (g/g) 1 hour | Absorption (g/g) 24 hours | Cohesion (category) |
|---|---|---|---|---|
| 1a | 0 | 29 | 56 | 1–2 |
| 1b | 10 | 37 | 55 | 2 |
| 1c | 20 | 22 | 50 | 2–3 |
| 1d | 30 | 21 | 31 | 3 |
| 1 | 50 | 12 | 12 | 4 |
| 1f | 80 | 8 | 8 | 5 |
| 1g | 100 | 4 | 4 | 5 |

*Of total acid content. The remaining acid content was lactic acid.

The dry modified chitosan fibres were relative soft and suitable for incorporation in wound care devices such as wound dressings.

Example 1a is showing, that the higher concentration of acetic acid used in the treatment of the fibres, the less absorbent and the more insoluble the fibres becomes. The optimal wound dressing has a maximum absorption, but just enough acid of the second type which gives the fibres insolubility, so the wound dressing can be removed in one piece from a wound.

Example 1b
Preparation of a Wound Dressing

A tow of sample 1c (non-sterile) was cut to 50 mm lengths and a wound dressing was formed by first carding the cut fibres to form an approximate 20 $g/m^2$ web, then cross folding the this web needling to provide a resultant non-woven fabric of approximately 100 $g/m^2$, then a 10 cm×10 cm square was cut to form the fabric. The fabric square was packaged and sterilised using an electron beam dose of 30 kGy.

The non-woven wound care product had an absorbency of 51 g/g and 0.52 $g/cm^2$.

Alternatively the tow itself may be cut for example to 40 cm lengths, packed and sterilised. Hereafter it may be used as a wound cavity filler.

Example 2a
Chitosan Fibres Treated with Acid and Heat

In a reaction vessel 200 grams of 96% ethanol was mixed with 150 mmole lactic acid. To this solution 20 grams of chitosan were added and the suspension was treated at the boiling point of the liquid for app. 4 hours under reflux. The fibres were then washed twice in ethanol. The sample was sterilised by 1*30 kGy electron beam. Hereafter the absorption and cohesion of the fibres were measured.

Table 2 is showing the absorption and cohesion of the sample (measured as triple measurements).

TABLE 2

| Sample No. | Absorption (g/g) 1 hour | Absorption (g/g) 24 hours | Cohesion (category) |
|---|---|---|---|
| 2 | 27 | 47 | 2 |

The modified fibres were soft and flexible and very suitable for wound dressings.

Example 2 demonstrates, that the amount of water has an limited influence on both the absorption and cohesion of the fibres, when they are treated at the boiling point of the ethanol. When the fibres are treated without additional water in the reaction vessel, the absorption decreases and the cohesion increases slightly.

Example 2b
Preparation of a Non-Wowen Fabric

A non-sterile sample of sample 2a was cut to 50 mm lengths and a wound care device was formed by first carding the cut fibres to form an approximate 20 $g/m^2$ web, then cross folding the web needling to give a resultant non-woven fabric of approximately 100 $g/m^2$, then a 10 cm×10 cm square was cut to form a fabric. The fabric was packed and sterilised using an electron beam dose of 30 kGy.

The non-woven wound care product had an absorbency of 49 g/g and 0.49 $g/cm^2$.

Alternatively, the tow itself is cut for example in 40 cm lengths, may be packed and sterilised. Hereafter it may be used as a wound cavity filler.

Example 3
Chitosan Fibres Treated with Acid at Low Temperature and Subsequently Heat Treated Solutions containing 50 gram 96% ethanol, 2.5 gram water and 35 mmole acid (mixtures of acetic and lactic acid) were prepared. To these solutions, 5 gram chitosan fibre sample was added and the samples were treated in the solutions at room temperature for 24 hours. Then the fibres were rinsed in 96% ethanol and dried. When the samples were dry, they were heat treated for 6 hours at 100° C. in an oven. Finally, the samples were sterilised by beta irradiation (1*30 kGy).

The absorption and cohesion of the samples were measured and the result is shown in Table 3 (based on triple measurements).

TABLE 3

| Sample No. | Mole % acetic acid* | Absorption (g/g) 24 hours | Cohesion (category) |
|---|---|---|---|
| 1a | 100 | 12 | 4 |
| 1b | 80 | 15 | 2 |
| 1c | 60 | 9 | 1 |
| 1d | 20 | 0 | 0 |
| 1 | 0 | 0 | 0 |

*Of total acid content. The remaining acid content was lactic acid.

This example also shows, that the optimal quantity of the first acid is not is the same for chitosan fibres treated with acid and a subsequently heat treatment, as for fibres treated with heat during the acid treatment. When the chitosan fibres are treated with acids at low temperature, with a subsequent heat treatment of 100° C., the amount of the first acid should be kept below 40%.

Example 4

Chitosan Fibres Treated with Acid at Low Temperature and a Subsequent Heat Treatment A solution containing 100 gram 96% ethanol, 5 gram water, 2 gram acetic acid and 0.8 gram 90% lactic acid was prepared. To this solution, 5 gram chitosan fibre sample was added and the sample was treated in the solution at room temperature for 1 hour. After the treatment the fibres were rinsed in 96% ethanol and dried. When the sample was dry, it was heat treated at different temperatures and periods in an oven. At last the samples were sterilised using beta irradiation (1*30 kGy).

Table 4a is showing the absorption after 24 hours of the samples heat treated at different temperatures and periods.

TABLE 4a

| Time | Temp. | | | |
|---|---|---|---|---|
| | 80° C. | 110° C. | 140° C. | 170° C. |
| 0 minute | | | 17 | |
| 1 minute | X* | X | X | 15 |
| 2 minutes | X | X | X | 16 |
| 5 minutes | X | X | X | 11 |
| 15 minutes | X | X | 18 | 11 |
| ½ hour | X | 15 | 11 | 9 |
| 1 hour | 14 | 15 | 9 | <10 |
| 2 hours | 13 | 16 | 16 | <10 |
| 4 hours | 12 | 15 | 12 | X |
| 8 hours | 13 | 15 | <10 | X |

*When X is stated, the absorption was not measured

Table 4b shows the cohesion of samples heat treated at different temperatures and times.

TABLE 4b

| Time | Temp. | | | |
|---|---|---|---|---|
| | 80° C. | 110° C. | 140° C. | 170° C. |
| 0 minute | | | 0–1 | |
| 1 minute | X* | X | X | 2–3 |
| 2 minutes | X | X | X | 3 |
| 5 minutes | X | X | X | 4 |
| 15 minutes | X | X | 3 | 4 |
| ½ hour | X | 3 | 3–4 | 4–5 |
| 1 hour | 2 | 3 | 4 | 5 |
| 2 hours | 3 | 3–4 | 4 | 5 |
| 4 hours | 3 | 3–4 | 4–5 | X |
| 8 hours | 3 | 4 | 5 | X |

*When X is stated, the cohesion was not measured

This example demonstrates, that when the fibres are acid treated at low temperature, a subsequent heat treatment is needed to make the modified chitosan fibres gelling and insoluble in water. If the fibres not are heat treated, they will dissolve when they contacted with water or exudate.

The more severe heat treatment the more water insoluble the chitosan fibres will become. There is also a tendency for less absorbent fibres using a severe heat treatment.

Example 5

The Influence of the Quantity of Acid in the Heat Treatment

In a reaction vessel 200 grams of 96% ethanol was mixed with 6 grams of water and different amounts of lactic acid (see table 5). To this solution 20 grams of chitosan fibres were added and the suspension was treated at the boiling point of the non-solvent for app. 4 hours under reflux. Then the fibres were washed twice in ethanol. The samples were sterilised by 1*30 kGy electron beam. Hereafter the absorption and cohesion of the fibres were measured.

Table 5 is showing the absorption and cohesion as a result of the quantity of acid in the combined acid and heat treatment (the results are a average of 3 measurements).

TABLE 5

| Sample No. | Gram 90% lactic acid in the solvent | Mmole lactic acid per gram chitosan | Absorption (g/g) | Cohesion (category) |
|---|---|---|---|---|
| 5a | 16 | 8 | 53 | 2 |
| 5b | 10 | 5 | 16 | 3–4 |
| 5c | 6 | 3 | 12 | 4 |

To obtain highly absorbent fibres, more than 5 mmole lactic acid per gram chitosan is needed. To obtain fibres with high cohesion, the amount of acid should be minimised to below 8 mmole lactic acid per gram chitosan.

Example 6

Use of Different Non-Solvents in the Acid Treatment

A sample was treated as in example 5a, except that 1-propanol or 1-butanol was used instead of 96% ethanol. Each non-solvent was prepared in such a manner, that there was 7 grams of water per 100 gram alcohol. The acid treatment was carried out at the boiling point of the non solvents for app. 4 hours. After the treatment the samples were washed and sterilised. The absorption and gellability were measured. The results can be seen in Table 6.

Table 6 is showing the absorption and cohesion as a results of the used non-solvent in the combined acid and heat treatment (the results are a average of 3 measurements).

TABLE 6

| Sample No. | Used non-solvent | Boiling point of non-solvent (° C.) | Absorption after 24 hours (g/g) | Cohesion (category) |
|---|---|---|---|---|
| 6a | Ethanol | 78 | 53 | 2 |
| 6b | 1-Propanol | 97 | 48 | 2–3 |
| 6c | 1-Butanol | 117 | 43 | 3 |

These results show, that the higher boiling point of the non-solvent, the lower cohesion of the modified chitosan fibres is obtained. The results demonstrates further, that when the fibres are treated in non-solvent with a high boiling point, the absorption is minimised, if the process time is constant.

Example 6a

Fibres Treated with a Limited Amount of Acid at an Elevated Temperature 70 grams of 96% ethanol were mixed in a container with 6.5 and 8.0 grams of lactic acid respectively. To this solution 10 grams of chitosan fibres were added. The container were sealed and placed in an autoclave (125° C. for 70 minutes). After the treatment the samples were washed and sterilised. The absorption and cohesion were measured. The results can be seen in Table 6a.

TABLE 6a

| Sample No. | Acid/chitosan (Mmole/g) | Absorption after 24 hours (g/g) | Cohesion (category) |
|---|---|---|---|
| 6aa | 8 | 48 | 2 |
| 6ab | 6.5 | 35 | 3 |

Table 6a shows that it is possible to convert chitosan fibres in a relatively short time by increasing the temperature and that the fibres becomes more cohesive by decreasing the level of acid per gram chitosan.

Example 7

4 grams of sample 5a (non-sterile) was mixed by carding with different quantities of calcium alginate fibres or carboxy methyl cellulose fibres. The fibre mixtures were sterilised (1*30 kGy). The absorption and cohesion of the sterile samples were measured.

Table 7 demonstrates the absorption and cohesion for fibre samples comprising mixtures of anionic and modified chitosan fibres (the results are averages of 3 measurements).

TABLE 7

| Sample No. | Type of anionic fibres | Quantity of anionic fibres (grams) | Absorption after 24 hours (g/g) | Cohesion (category) |
|---|---|---|---|---|
| 7a | Calcium Alginate | 4 | 36 | 3 |
| 7b | CM-Cellulose | 4 | 35 | 3 |
| 7c | CM-Cellulose | 1 | 34 | 3 |

This example shows, that if the chitosan fibres are mixed with alginate or carboxy methyl cellulose fibres, the cohesion of the fibres increases, while the absorption decreases.

Example 8
Chitosan Fibres Treated with Acid at Low Temperature and a Subsequent Heat Treatment A solution containing 100 gram 96% ethanol, 5 gram water, 6.4 gram 90% lactic acid and 1.0 gram acetic acid was prepared. To this solution, 10 grams of chitosan fibres were added and the sample were treated in the non-solvent at room temperature for 1 hour. After the treatment the fibres were rinsed in 96% ethanol and dried at 30° C. When the samples were dry, the sample was treated with heat. The heat treatment was carried out at different temperatures and periods in an oven. After the heat treatment the samples were sterilised using beta irradiation (1*30 kGy).

Table 8a demonstrates the absorption and cohesion (absorption (g/g)/cohesion) of the samples heat treated at different temperatures and periods (measured as a triple measurement on sterile samples).

TABLE 8

| | Temp. | | |
|---|---|---|---|
| Time | 110° C. | 135° C. | 160° C. |
| 0 minute | | | soluble |
| 2 minutes | x | x | soluble |
| 8 minutes | x | soluble | 44/2 |
| 20 minutes | x | soluble | 40/2–3 |
| 1 hour | 10/1 | 27/2 | 17/4 |
| 4 hours | 10/1 | 23/3–4 | x |

The results demonstrate, that the higher temperature the subsequent heat treatment is processed at, the higher absorption is obtainable. Also the duration of the heat treatment is influenced by the heat treatment (the higher temperature, the shorter time is needed to obtain insoluble fibres).

Example 9
Chitosan Fibres Treated with Different Quantities of Acid at Low Temperature and a Subsequent Heat Treatment The samples were processed as in Example 8, but with following adjustment:

In Example 9a the only used acid was lactic acid (8 gram 90% lactic acid per 10 gram chitosan), and in Example 9b the acid volumes were 4.8 grams 90% acetic acid and 2 grams acetic acid.

After acid treatment both samples were heat treated at 160° C. for 10 minutes. Hereafter the absorption and cohesion was measured.

The absorption and cohesion result are listed in Table 9.

TABLE 9

| Sample No. | Absorption after 24 hours (g/g) | Cohesion (category) |
|---|---|---|
| 9a | 43 | 2 |
| 9b | 27 | 3 |

This example is showing, that when the chitosan fibres are modified in a two step process (acid treatment at room temperature and subsequently a heat treatment), only one acid is needed to obtain fibres with cohesion enough to removal in one piece is possible. The example also demonstrates, that the more acetic acid in the treatment, the higher cohesion is obtained, but the absorption decreases with increasing amounts of acetic acid.

Example 10
Preparation of a Woven Fabric Comprising Chitosan Fibres

The modified chitosan fibres (sample 9a in Example 9) were processed into yarn, and a woven fabric was made. The material was cut in squares of 10*10 cm², packed and sterilised.

The woven fabric is suitable as a wound care device, to cover and gel upon a wound site while absorbing a high amounts of wound exudate.

Example 11
Preparation of a Woven Fabric Comprising Chitosan Fibres and Cotton

The modified chitosan fibres (sample 9a in Example 9) were processed into yarn and weaved with cotton to produce a woven fabric (40% chitosan and 60% cotton). The material was cut in squares of 10*10 cm², packed and sterilised.

The woven fabric is suitable as a non adherent wound dressing to place directly on a wound and protect the wound against the secondary wound dressing and from drying out.

Figure 1:
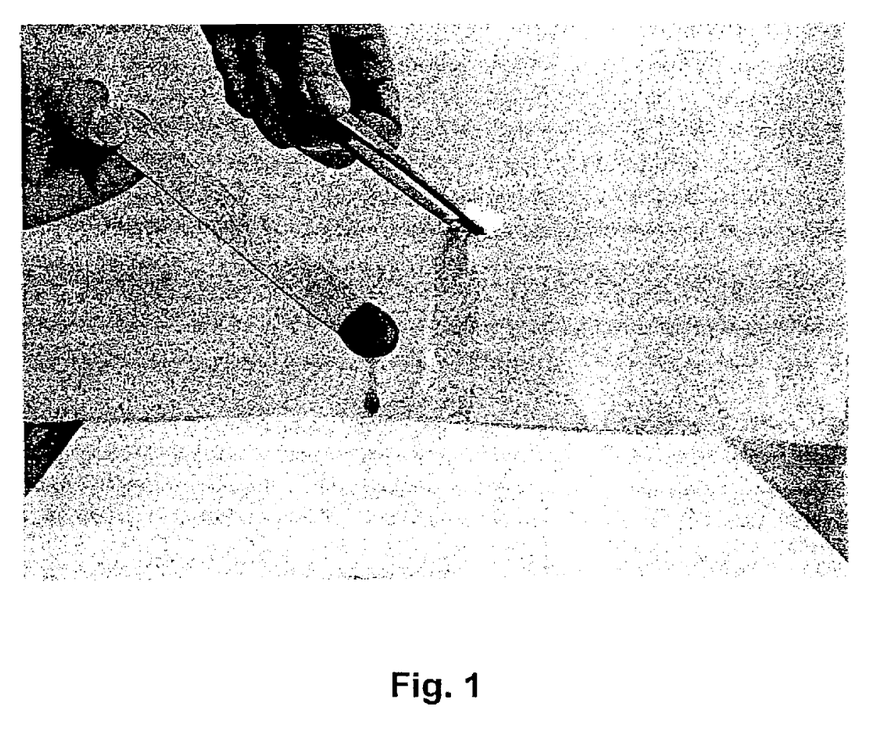
FIG. 1 A photograph comparing chitosan fibers of the present invention to powdered chitosan treated using a similar method.

Example 12
Comparing Treated Fibres and Powder 10 grams of chitosan powder was treated as the fibres in sample 1c (but not sterilised). FIG. 1, a colour photo, shows the difference in cohesion between powders and the fibres prepared according to this invention (the fibres and powder are treated exactly the same way and both samples are non-sterile). The FIGURE shows both the fibres from sample 1c (non-sterile) and the powder prepared as sample 1c.

The powder is discrete insoluble absorbent particles, while the fibres turns into a cohesive mass. Thus, this example demonstrate that the cohesion may only be obtained by the use of fibres, while the same effect will not be achieved by using powderous chitosan. The powder particles are not suitable as the main ingredient in a wound care product if removal in one piece is desired, while the fibres indeed are useful as the main ingredient in a wound care device.

Example 13
The Maximum Absorbency of Some Selected Fibres From the Earlier Examples The maximum absorbency is measured after 3 days in solution A after the same method as absorption after 24 hours. The absorption is measured on non-sterile samples.

TABLE 13

| Sample no. | Absorption after 24 hours (g/g) | Maximum absorption (g/g) | Cohesion (category) |
|---|---|---|---|
| 5a | 53 | 70 | 2 |
| 6b | 48 | 47 | 3 |

This example is showing that the absorption is increasing in up to 3 days when the cohesion is evaluated to 2. If the cohesion is evaluated to 3, the maximum absorption is reached within the first 24 hours. Samples with lower cohesion may have higher absorption. This is due to the samples swellability, which is higher, when the sample is less cohesive.

Example 13b

A non-sterile sample of sample 5a and of 6b was cut to app. 50 mm lengths and a wound dressing was formed by first carding the cut fibres to form an approximate 20 g/m² web, then cross folding the this web needling to give a resultant non-woven fabric of approximately 100 g/m², then a 10 cm×10 cm square was cut to form the fabric. The square of the fabric was packaged and sterilised using an electron beam dose of 30 kGy.

The sterile non-woven wound care device of sample 5a had an absorbency of 60 g/g and 0.59 g/cm².

The sterile non-woven wound care device of sample 6b had an absorbency of 46 g/g and 0.48 g/cm². The wound care device is easily removed in one piece from a exuding wound.

Example 14
Prolonged Acid Treatment

A sample was treated as sample 1a, but the acid treatment was prolonged to 10 hours instead of 4 hours.

The absorption and cohesion is listed in table 14 (as a average of triple measurements).

TABLE 14

| Sample no. | Absorption after 24 hours (g/g) | Absorption after 3 days (g/g) | Cohesion (category) |
|---|---|---|---|
| 14 | 55 | 74 | 2 |

This example demonstrates, that only one add is needed in the acid treatment when the is conducted at the boiling point of ethanol (below 85° C.). It is possible to prepare modified chitosan fibre samples with extremely high absorption compared to prior art.

Example 15

This example demonstrates the method of making superabsorbent gellable, substantially water insoluble modified chitosan fibres by partly carboxy methylating the chitosan fibres. A solution containing 100 gram water, 15 gram sodium hydroxide, 45 gram sodium chloro acetate and 100 gram of ethanol was prepared. 10 grams of chitosan fibres were added to the solution and the solution was heated to the boiling point of the solution and treated until the fibres was partly carboxy methylated. After the treatment, the modified chitosan fibres was washed in an alcohol bath containing an acid. The fibres were finally dried.

The fibres were processed into an sterile non-woven fabric (as in example 1b).

What is claimed is:

1. A method of preparation of a wound care device comprising chitosan being capable of absorbing liquid to form a swollen, coherent gel, said method comprises the steps of:
   a) suspending the chitosan in the form of fibers in a non-solvent comprising acid;
   b) isolating the resulting modified chitosan fibers from the non-solvent; and
   c) treating the chitosan fibers with heat during step a) or/and b).

2. A method of preparation of a wound care device according to claim 1, characterized in that the fibers are manufactured into a fiber rope, knitted, woven or non-woven sheet or fabric.

3. A wound care device made by the method of claim 2.

4. A method of preparation of a wound care device according to claim 1, characterized in that the acid is an hydroxy or acyl organic acid, which is soluble in the solvent used, preferably glycolic, glyoxylic, pyruvic, lactic or a hydroxy propionic/butanic acid.

5. A wound care device made by the method of claim 4.

6. A method of preparation of a wound care device according to claim 1, characterized in that the heat treatment of the chitosan is carried out at a temperature of about 50–250° C.

7. A wound care device made by the method of claim 6.

8. A wound care device made by the method of claim 1, characterized in that the device comprises from 0–60% of fibers other than chitosan.

9. A method of preparation of a wound care device according to claim 1, characterized in that the acid is a mixture of at least two acids.

10. A wound care device made by the method of claim 9.

11. A method of preparation of a wound care device according to claim 1, characterized in that the ratio of acid to chitosan is from 2 mmol to 20 mmol acid per gram chitosan.

12. A wound care device made by the method of claim 11.

13. A method of preparation of a wound care device according to claim 1, characterized in that the ratio of acid to chitosan is 2 to 7.5 mmol acid per gram chitosan.

14. A wound care device made by the method of claim 13.

15. A wound care device made by the method of claim 1.

* * * * *